US010702672B2

(12) United States Patent
Lampropoulos et al.

(10) Patent No.: US 10,702,672 B2
(45) Date of Patent: Jul. 7, 2020

(54) PRESSURE-SENSING CATHETERS AND RELATED METHODS

(71) Applicant: Merit Medical Systems, Inc., South Jordan, UT (US)

(72) Inventors: Fred Lampropoulos, Salt Lake City, UT (US); Nicholas Accisano, III, Howell, NJ (US); Jim Mottola, West Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 307 days.

(21) Appl. No.: 15/053,683

(22) Filed: Feb. 25, 2016

(65) Prior Publication Data

US 2016/0250444 A1  Sep. 1, 2016

Related U.S. Application Data

(60) Provisional application No. 62/121,606, filed on Feb. 27, 2015, provisional application No. 62/278,803, filed on Jan. 14, 2016.

(51) Int. Cl.
*A61B 5/02* (2006.01)
*A61M 25/00* (2006.01)
(Continued)

(52) U.S. Cl.
CPC ..... *A61M 25/0026* (2013.01); *A61B 5/02158* (2013.01); *A61M 25/0108* (2013.01);
(Continued)

(58) Field of Classification Search
CPC ...... A61M 2025/0003; A61M 25/0026; A61M 25/0108; A61M 2025/0039;
(Continued)

(56) References Cited

U.S. PATENT DOCUMENTS 4,777,951 A * 10/1988 Cribier .............. A61M 25/0023
                                                    600/485
5,558,635 A *  9/1996 Cannon ............. A61M 25/0169
                                                    604/264
(Continued)

FOREIGN PATENT DOCUMENTS

WO     199836790     8/1998
WO     2003037420    5/2003
(Continued)

OTHER PUBLICATIONS

International Search Report and Written Opinion dated Jul. 25, 2016 for PCT/US2016/019564.
(Continued)

*Primary Examiner* — Navin Natnithithadha
*Assistant Examiner* — Andrey Shostak
(74) *Attorney, Agent, or Firm* — Stoel Rives LLP

(57) ABSTRACT

A multi-lumen catheter can be used to measure pressure at multiple locations within the vasculature. The multi-lumen catheter can include multiple segments, such as a proximal portion, an intermediate portion, and a distal portion. A segment of a multi-lumen catheter may differ from another segment of the same multi-lumen catheter in radiodensity, hardness, and/or some other characteristic. Some multi-lumen catheters are designed to permit measurements of pressure in different lumens.

18 Claims, 11 Drawing Sheets

(51) Int. Cl.
*A61B 5/0215* (2006.01)
*A61M 25/01* (2006.01)
*A61B 5/00* (2006.01)
*A61B 90/00* (2016.01)

(52) U.S. Cl.
CPC .......... *A61B 5/6853* (2013.01); *A61B 5/6855* (2013.01); *A61B 5/6857* (2013.01); *A61B 2090/065* (2016.02); *A61M 2025/0002* (2013.01); *A61M 2025/0003* (2013.01); *A61M 2025/0036* (2013.01)

(58) Field of Classification Search
CPC .......... A61M 25/0043; A61M 25/0054; A61M 2025/0034; A61M 25/0023; A61M 25/0021; A61M 25/0009; A61M 25/001; A61M 25/0004; A61M 2025/0036; A61M 2025/0002; A61B 5/6857; A61B 5/02158; A61B 5/6855; A61B 5/6853; A61B 2090/065

See application file for complete search history.

(56) References Cited

U.S. PATENT DOCUMENTS

| | | | | |
|---|---|---|---|---|
| 5,718,678 A * | 2/1998 | Fleming, III | ..... | A61M 25/0009 604/43 |
| 5,775,327 A * | 7/1998 | Randolph | ......... | A61M 25/0054 600/374 |
| 5,795,325 A * | 8/1998 | Valley | .............. | A61B 17/12022 604/103.1 |
| 5,862,803 A * | 1/1999 | Besson | .............. | A61B 5/14552 128/903 |
| 6,325,790 B1 * | 12/2001 | Trotta | ................... | A61L 29/049 600/433 |
| 2002/0010411 A1 * | 1/2002 | Macoviak | .......... | A61M 25/1002 604/8 |
| 2002/0087156 A1 | 7/2002 | Maguire et al. | | |
| 2002/0095203 A1 * | 7/2002 | Thompson | ................ | A61F 2/95 623/1.11 |
| 2004/0116901 A1 | 6/2004 | Appling | | |
| 2005/0203425 A1 * | 9/2005 | Langston | ........... | A61B 5/02158 600/485 |
| 2005/0228308 A1 * | 10/2005 | Iddan | ..................... | A61B 1/041 600/561 |
| 2011/0060229 A1 * | 3/2011 | Hulvershorn | ........ | A61B 5/0215 600/486 |
| 2015/0231377 A1 * | 8/2015 | Tierney | ............... | A61M 27/008 604/544 |

FOREIGN PATENT DOCUMENTS

| | | |
|---|---|---|
| WO | 2005028015 | 3/2005 |
| WO | 2014125497 | 8/2014 |

OTHER PUBLICATIONS

Extended European Search Report dated Sep. 24, 2018 for EP16756357.6.

* cited by examiner

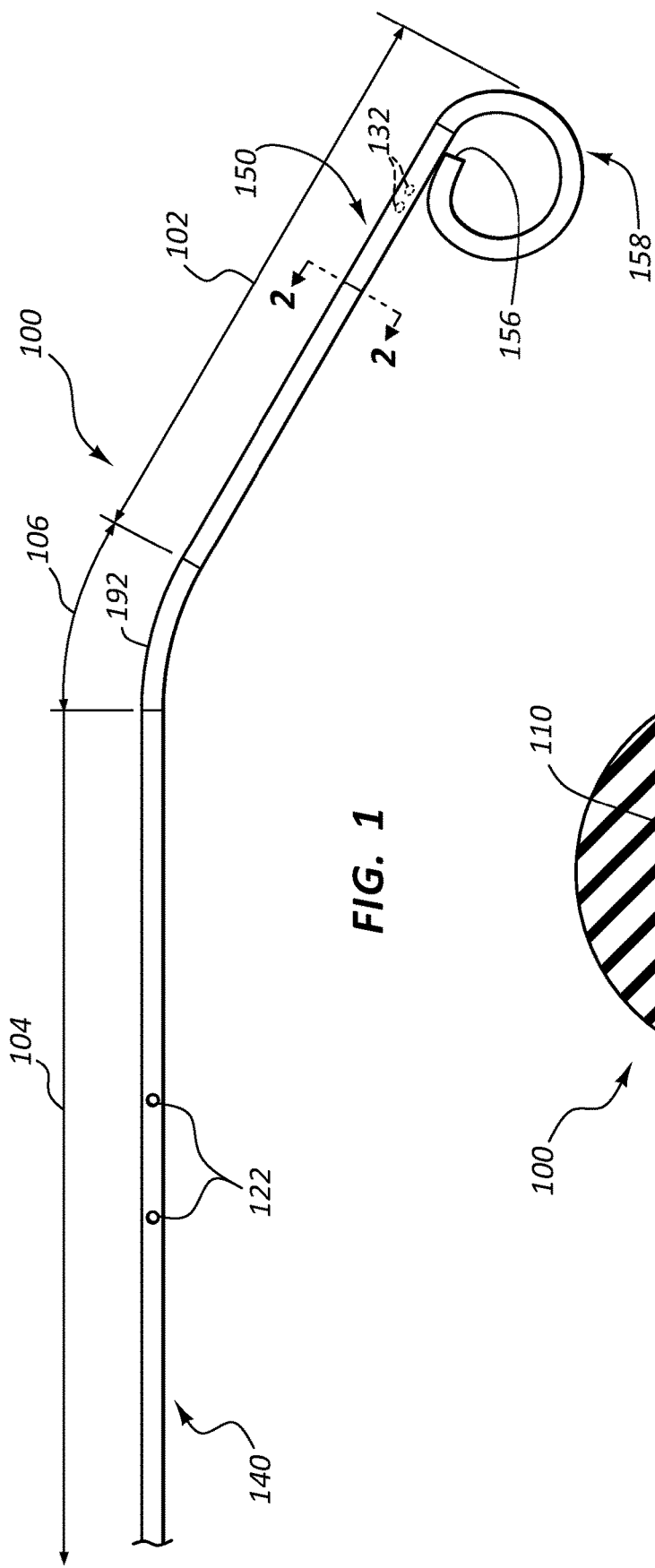
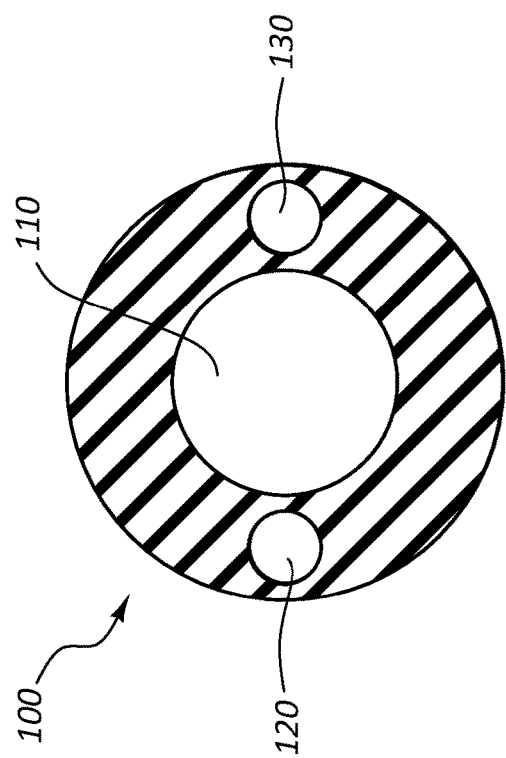

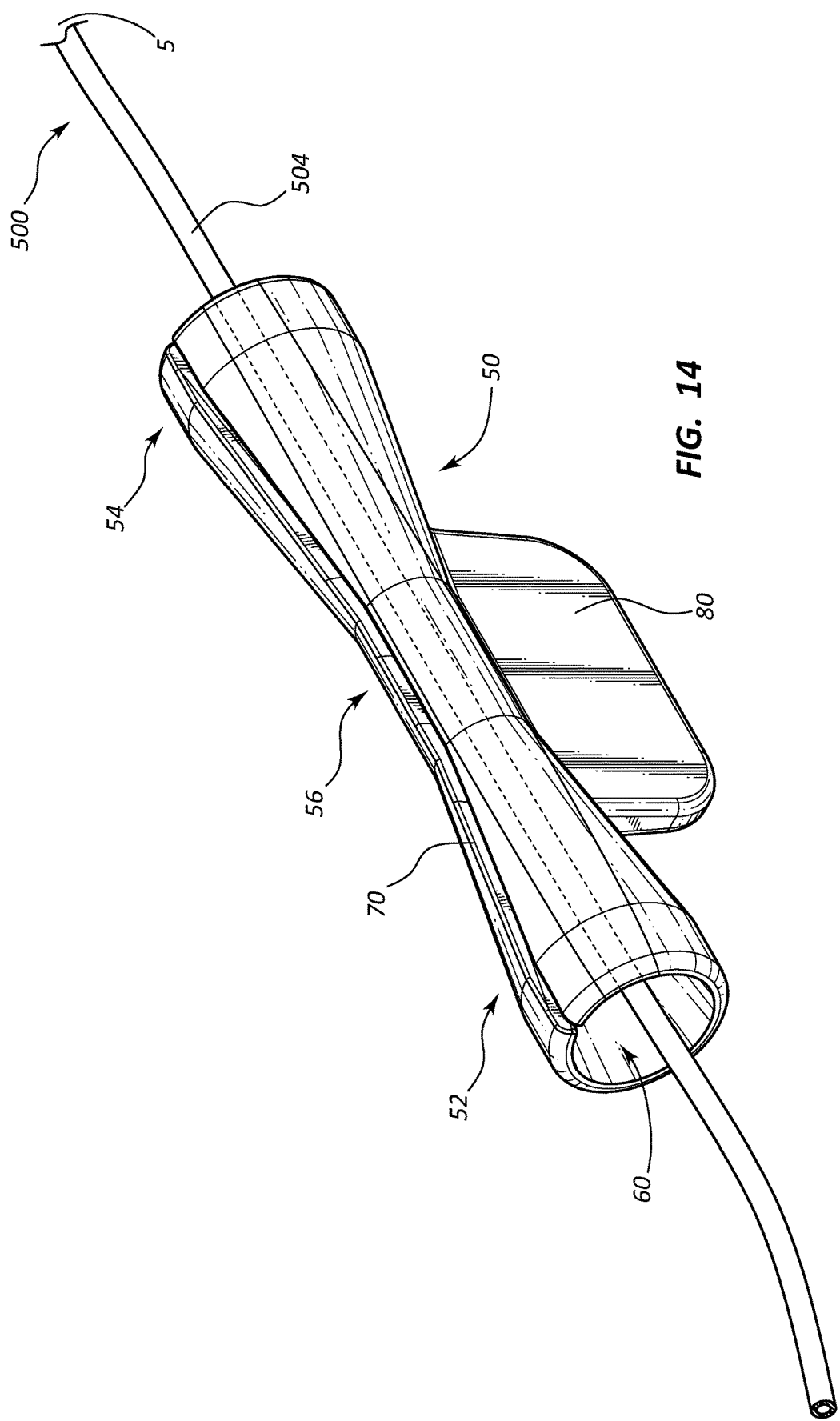

PRESSURE-SENSING CATHETERS AND RELATED METHODS

RELATED APPLICATIONS

This application claims priority to U.S. Provisional Application No. 62/121,606 filed on Feb. 27, 2015 and titled "Pressure Sensing Catheters and Related Methods," and U.S. Provisional Application No. 62/278,803 filed on Jan. 14, 2016 and titled "Pressure-Sensing Catheters and Related Methods," both of which are hereby incorporated by reference in their entireties.

TECHNICAL FIELD

This application generally relates to medical devices. More particularly, this application relates to multi-lumen catheters, such as multi-lumen catheters for sensing pressures or differences in pressure. Other uses of multi-lumen catheters are also contemplated.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 1 is a side view of a portion of an embodiment of a catheter.

FIG. 2 is a cross-section of the tip portion of the catheter of FIG. 1 taken along the line 2-2 of FIG. 1.

FIG. 14 is a perspective view of a gripping member for manipulating a catheter that has been partially inserted into a patient.

DETAILED DESCRIPTION

Figure 3:
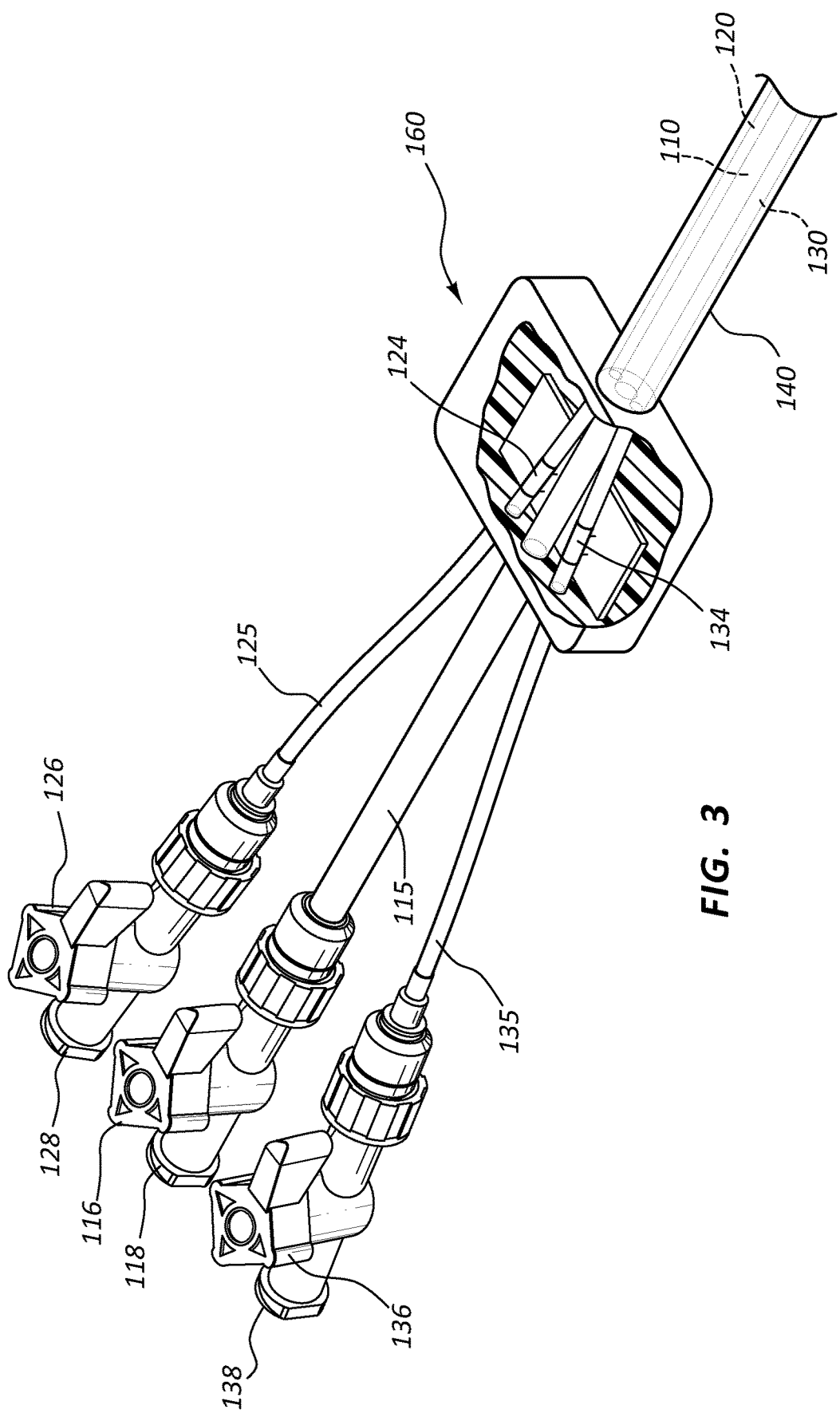
FIG. 3 is a perspective view of an embodiment of a proximal end of a catheter with a cutaway illustrating embodiments of pressure sensors in communication with the separate lumens of the catheter of FIG. 1.

Multi-lumen catheters for sensing and/or measuring pressure or other characteristics are disclosed herein, along with related methods.

For example, in some embodiments, a catheter comprises one or more side ports or other openings that are configured to allow body fluid from a first region of a patient's body to enter into a first lumen of the catheter. The catheter may also comprise one or more side ports or other openings that are configured to allow body fluid to enter into a second lumen from a second region that is distinct from the first region. The first and second lumens may be configured to be coupled to one or more sensors (e.g., pressure sensor(s), pH sensor(s), or temperature sensor(s)) that detect and/or measure the fluid pressure or facilitate the determination of other characteristics of fluid disposed within the lumens (e.g., pH, temperature). In some embodiments, the sensor may be incorporated within the catheter, delivered through a catheter lumen, and/or disposed adjacent a proximal end of a catheter lumen. A catheter with a first lumen and a second lumen that are in primary fluid communication with fluid from different regions of a patient's body may facilitate the determination of differences in blood pressure or other characteristics at the two regions.

For example, a catheter may be configured to detect and/or measure differences in blood pressure across an obstruction or valve. In an exemplary embodiment, a multi-lumen catheter that includes multiple ports and/or other openings may be inserted into a patient such that a first lumen is in primary fluid communication with fluid on one side of the valve and a second lumen is in primary fluid communication with fluid on the other side of the valve. By coupling each lumen to one or more pressure sensors, the difference in blood pressure across a valve may be determined. Measuring the difference in blood pressure across a valve may be particularly important in connection with procedures relating to the function of heart valves, such as valvuloplasty. For example, during a valvuloplasty procedure (or other medical procedure), differences in blood pressure across a valve may be determined by placing a first lumen in primary fluid communication with fluid in a ventricle on one side of a valve (e.g., a semilunar valve) and a second lumen in primary fluid communication with fluid in the aorta.

A multi-lumen catheter may alternatively or additionally be configured to measure the flow rate of a fluid within a lumen. For example, a cold fluid may be delivered through a first lumen of a catheter to an upstream location within a patient while a thermister or other temperature sensor may be delivered through a second lumen or otherwise disposed at a downstream location. By measuring the change in temperature over a period of time subsequent to delivery of the cold fluid, the flow rate of the fluid may be estimated or determined.

A multi-lumen catheter may alternatively or additionally be configured to monitor or deliver an electrical pulse. For example, a first electrode may be delivered through a first lumen of a catheter to a first location within a patient and a second electrode may be delivered to a second location within a patient. Disposed in this manner, the electrodes may be used to monitor or deliver one or more electrical pulses. More particularly, electrodes disposed in this manner may be used to monitor electrical pulses across a heart or to function as a defibrillator or pacemaker by delivering one or more electrical pulses to the heart.

Some multi-lumen catheters may additionally or alternatively be used both to deliver fluids and/or solids through a first lumen and to detect and/or measure fluid pressure or other fluid characteristics through a second lumen. For example, a catheter may comprise a first lumen that is configured to deliver medicaments, contrast agents, medical devices and/or other materials and a second lumen that is configured to detect and/or measure fluid pressure (e.g., blood pressure). In some embodiments, delivery through a first lumen and fluid pressure detection or measurement through a second lumen may occur simultaneously. In some embodiments, the flow rate and/or pressure of fluid delivered through the first lumen may be controlled and/or monitored to ensure proper delivery of the fluid.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities. Two components may be coupled to each other even though they are not in direct contact with each other. The phrase "fluid communication" is broad enough to refer to arrangements in which a fluid (e.g., a gas or a liquid) can flow from one element to another element when the elements are in fluid communication with each other. The directional terms "proximal" and "distal" are used herein to refer to opposite locations on a component or device. The proximal end of a component or device is defined as the end of the device closest to the practitioner when the device is in normal use by the practitioner. The distal end is the end opposite the proximal end, along the longitudinal direction of the device, or the end farthest from the practitioner during normal use. Unless otherwise stated, all ranges include both endpoints and all numbers between the endpoints. Two components may be "coaxial" even if the components adopt a non-linear conformation. For example, a second tube may be coaxially disposed within a first tube that adopts a non-linear conformation if the second tube remains centrally disposed within the first tube.

Turning now to the figures, FIG. 1 illustrates an exemplary embodiment of a catheter 100 with a separate lumen and pressure sensor. FIG. 2 illustrates a cross-section of a tip portion 150 of catheter 100 taken along the line 2-2 of FIG. 1. The catheter 100 comprises a main lumen 110, a first separate lumen 120 configured for low-volume fluid flow as compared to the main lumen 110, and a second separate lumen 130 configured for low-volume fluid flow as compared to the main lumen 110. For example, the main lumen 110 may be configured to withstand high pressure injections in the range of about 1000 psi, whereas the first and second separate lumens may be configured to withstand high pressure injections in the range of about 100 to about 200 psi. In the illustrated embodiment, the first separate lumen 120 and the second separate lumen 130 have the same diameter. It should be understood that the diameter of the first and second separate lumens 120, 130 may be the same as or different from each other and any additional separate lumens. Additionally, some or all of the lumens may be used for sampling patient fluids.

The catheter 100 further comprises two proximal ports 122 formed in an outer surface of the catheter 100, the two proximal ports 122 in communication with the first separate lumen 120. The catheter 100 further comprises two distal ports 132 formed in the outer surface, the two distal ports 132 in communication with the second separate lumen 130. The two distal ports 132 are shown in phantom (visible from the underside of catheter 100 as oriented in FIG. 1).

In catheter 100, the first separate lumen 120 is opposite the second separate lumen 130 (i.e., located on opposing sides of the main lumen 110). Therefore, the two distal ports 132 are on the opposite side from the two proximal ports 122. It should be understood that in other embodiments the first and second separate lumens 120, 130 may be oriented relative to the main lumen 110 in a variety of ways and this will affect where the two distal ports 132 are formed relative to the two proximal ports 122. Additionally, the first and second separate lumens 120, 130 are illustrated as outer lumens relative to the main lumen 110, but there could be other configurations where the main lumen 110 is an outer lumen.

The outer surface of the catheter 100 may be made of a unitary material. For example, the body portion 140 and the tip portion 150 of catheter 100 may be manufactured as a single piece, such as via extrusion. The tip portion 150 includes a curved distal region 158 (e.g., a pigtail) and terminates at the distal end 156. The curved distal region 158 may be manufactured as part of the rest of the tip portion 150 or may be manufactured separately and later attached.

In some embodiments, the main lumen 110 extends through the distal end 156, but the first and second separate lumens 120, 130 do not. For example, the first separate lumen 120 may only extend from the proximal end of the catheter 100 to a point sufficiently past the two proximal ports 122 to allow fluid to enter the two proximal ports 122 and the first separate lumen 120. Likewise, the second separate lumen 130 may only extend from the proximal end of the catheter 100 to a point sufficiently past the two distal ports 132 to allow fluid to enter the two distal ports 132 and the second separate lumen 130.

One of ordinary skill in the art, having the benefit of this disclosure, will recognize that a variety of additional features may be included in the catheter 100. For example, a balloon, a stent, or both, may be located between the two proximal ports 122 and the two distal ports 132. In embodiments where a balloon is present, the main lumen 110 may be used to inflate and deflate the balloon. In such embodiments, the main lumen 110 may not extend through the distal end 156. Instead, the main lumen 110 may terminate prior to the distal end 156 or be capped at the distal end 156.

As shown in FIG. 1, the catheter 100 may include a distal portion 102, a proximal portion 104, and an intermediate portion 106 disposed between the proximal portion 104 and the distal portion 102. The distal portion 102 may have at least one port (e.g., distal ports 132) that is in fluid communication with a first lumen (e.g., second separate lumen 130) of the catheter 100. The proximal portion 104 may have at least one port (e.g., proximal ports 122) that is in fluid communication with a second lumen (e.g., first separate lumen 120) of the catheter 100.

In some embodiments, the distal portion 102 extends from a distal end 156 of the catheter 100 to the intermediate portion 106 of the catheter 100. The intermediate portion 106 of the catheter may extend from the proximal end of the distal portion 102 to the distal end of the proximal portion 104. The proximal portion 104 may extend from the proximal end of the intermediate portion 106 to adjacent the proximal end of the catheter 100. In some embodiments, the intermediate portion 106 includes a bend 192 when the catheter 100 is in an unconstrained state.

The distal portion 102 may have a first radiodensity, the proximal portion 104 may have a second radiodensity, and the intermediate portion 106 may have a third radiodensity.

In some embodiments, the third radiodensity differs from both the first radiodensity and the second radiodensity. For example, in some embodiments, the intermediate portion 106 is less radiodense than both the distal portion 102 and the proximal portion 104. In other embodiments, the intermediate portion 106 is more radiodense than both the distal portion 102 and the proximal portion 104. In some embodiments, the radiodensity of the distal portion 102, the proximal portion 104, and the intermediate portion 106 are each different from one another. In other embodiments, the radiodensity of the distal portion 102 and the proximal portion 104 are substantially the same.

Some embodiments in which the radiodensity of the intermediate portion 106 differs from the radiodensity of both the proximal portion 104 and the distal portion 102 may facilitate proper placement of the catheter 100 during an interventional procedure. For example, the catheter 100 may be inserted into a patient to measure pressure differences across a heart valve during a medical procedure. As the practitioner inserts the catheter 100 into the patient and toward the heart valve, the location of the catheter 100 may be tracked by radiographic imaging. More particularly, the practitioner may advance the catheter 100 within the patient while viewing radiopaque portions of the catheter 100 until the proximal portion 104 of the catheter 100 is disposed proximal of the valve while the distal portion 102 of the catheter 100 is disposed distal of the valve. For example, in some embodiments in which the proximal portion 104 and distal portion 102 have a greater radiodensity than the intermediate portion 106, the practitioner may, as determined by radiographic imaging, advance the catheter 100 within the patient until the radiopaque distal portion 102 is disposed distal of the valve, the radiolucent intermediate portion 106 is disposed across the valve, and the radiopaque proximal portion 104 is disposed proximal of the valve.

In some embodiments, one or more portions of the catheter 100 may be of different hardness, such as described in further detail below in connection with FIGS. 6-11. In other embodiments, each portion of the catheter 100 may be of substantially the same hardness.

Figure 4:
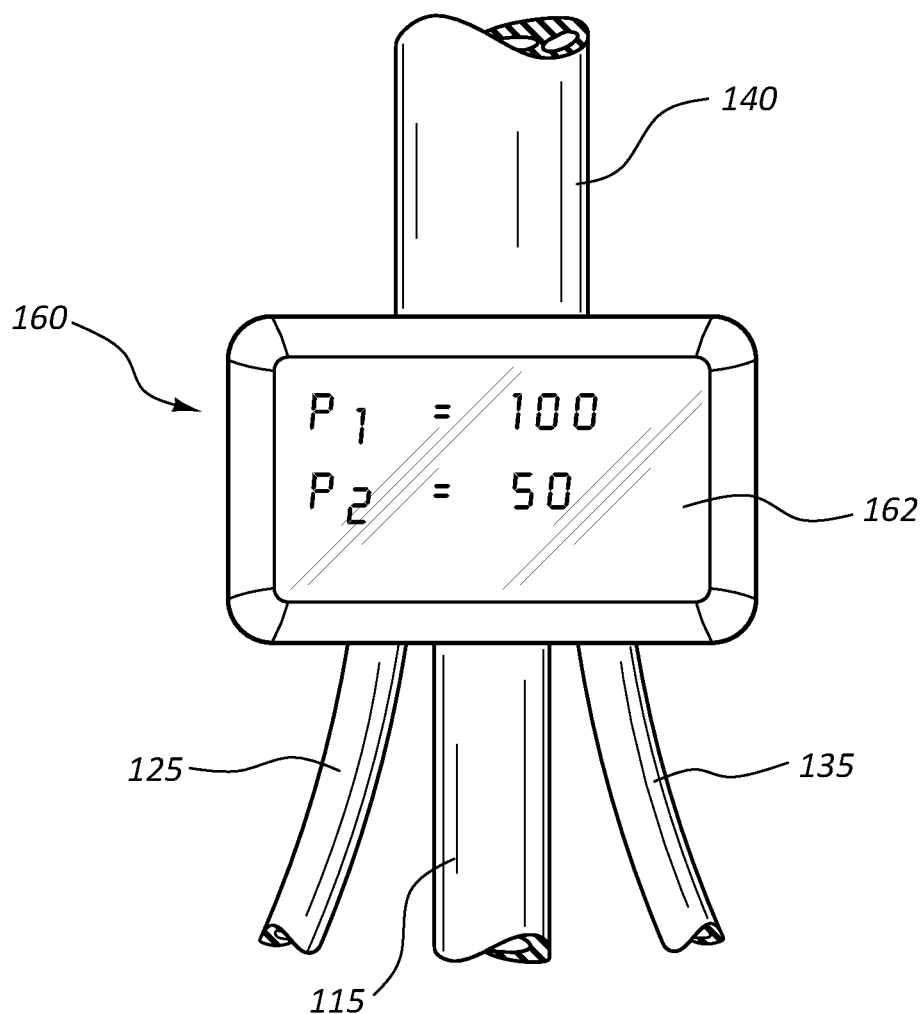
FIG. 4 is a top view of one embodiment of a single pressure readout device located near the proximal end of the catheter of FIG. 1.

FIG. 1 does not illustrate the proximal end of the catheter 100. FIG. 3 and FIG. 4 illustrate the proximal end of the catheter 100. The proximal end of the body portion 140 of the catheter 100 terminates in a main proximal tube 115, first separate tube 125, and second separate tube 135. Each of the tubes 115, 125, 135 terminates in a valve 116, 126, 136 (respectively) and a luer connection 118, 128, 138 (also respectively). The valves and luer connections may be sized and selected to handle the flowrates and pressures of their respective lumens. One of ordinary skill in the art, having the benefit of this disclosure, will recognize that the proximal end of the catheter 100 may terminate in a variety of different plumbing configurations.

As illustrated in FIG. 3, the catheter 100 includes a first inline pressure sensor 124 in communication with the first separate lumen 120, and a second inline pressure sensor 134 in communication with the second separate lumen 130. As illustrated, the first and second inline pressure sensors 124, 134 may comprise pressure transducers. The pressure transducers may comprise a metal band that expands or contracts with changes in the first and second separate tubes 125, 135, respectively. Expansions or contractions in the metal may change the electrical resistance in the metal, which correlates with changes in pressure within the lumens. One of ordinary skill in the art, having the benefit of this disclosure, will recognize that a variety of pressure transducers in different configurations, as well as other types of pressure sensors, could be used.

As illustrated in FIG. 3 and FIG. 4, the catheter 100 includes a single pressure readout device 160 located near the proximal end of the catheter 100. The single pressure readout device 160 is in communication with the first inline pressure sensor 124 and the second inline pressure sensor 134. The first inline pressure sensor 124, the second inline pressure sensor 134, and the single pressure readout device 160 are integrated in a single device. The single pressure readout device 160 comprises a display 162 configured to display the pressure of the first separate lumen 120 (e.g., 100 millimeters of mercury ("mm Hg")) and the pressure of the second separate lumen 130 (e.g., 50 mm Hg).

In alternative embodiments, instead of a single pressure readout device 160, there may be a first pressure readout device located at or near a proximal end of the catheter 100 and in communication with the first inline pressure sensor 124. The first inline pressure sensor 124 and the first pressure readout device may be integrated in a single device. Likewise, there may be a second pressure readout device located at or near a proximal end of the catheter 100 and in communication with the second inline pressure sensor 134. In some embodiments, the second inline pressure sensor 134 is not present.

Additionally, the single pressure readout device 160 may not be present. Instead, the first inline pressure sensor 124 and second inline pressure sensor 134 (if present) may communicate (wirelessly or otherwise) with a separate device, such as a desktop, tablet, smartphone, monitoring station, etc.

The single pressure readout device 160 (or one of the alternative readout devices discussed above) may be configured to track a pressure wave form generated by the first and second inline pressure sensors 124, 134 and/or differences between the pressures.

Additionally, the catheter 100 may include additional pressure sensors located at different locations along the first and second separate lumens 120, 130. In such embodiments, the single pressure readout device 160 (or one of the alternative readout devices discussed above) may be configured to indicate occlusion of the first separate lumen 120, the second separate lumen 130, or both.

The catheter 100 may also include other types of sensors in addition to the inline pressure sensors (such as, for example, pH sensors, electrical sensors, and temperature sensors). The catheter 100 may also include therapeutic elements such as pacing electrodes, antennae or other elements.

The main lumen 110 may be defined by a material configured to withstand high pressure. For example, the main lumen 110 of the tip portion 150 may be defined by a braid-reinforced main lumen or tubular-shaped polyimide liner that extends the length of the tip portion 150. Alternatively, the tubular-shaped polyimide liner may extend the entire length of the catheter 100. In either example, the polyimide liner may be unperforated along the tip portion 150. When the tubular-shaped polyimide liner extends the entire length of the catheter 100, the liner may be unperforated along the entire length. The remainder of the catheter 100 may be made from a polyether block amide, such as, for example, PEBAX.

Figure 5:
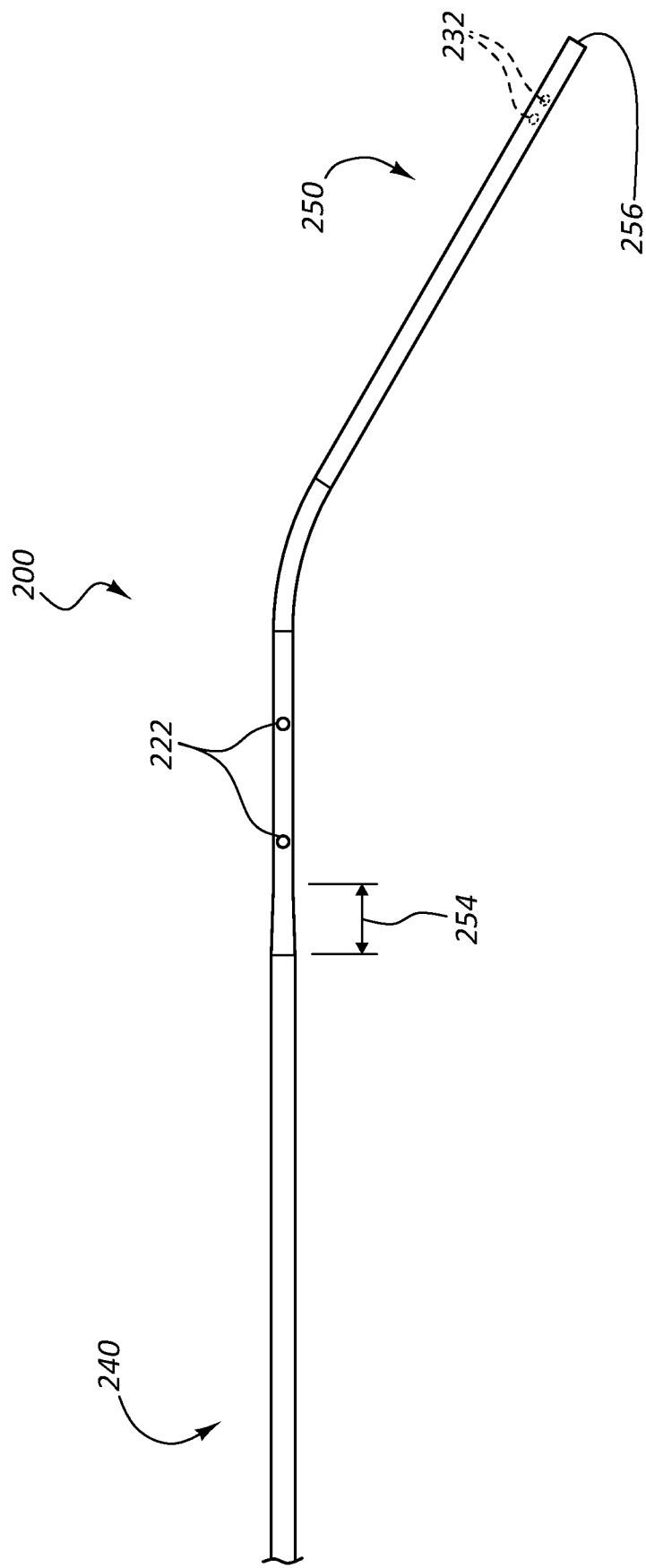
FIG. 5 is a side view of a portion of another embodiment of a catheter.

FIG. 5 depicts an embodiment of a catheter 200 that resembles the catheter 100 described above in certain respects. Accordingly, like features are designated with like reference numerals, with the leading digits incremented to "2." For example, the embodiment depicted in FIG. 5 includes a body portion 240 that may, in some respects, resemble the body portion 140 of FIGS. 1-4. Relevant disclosure set forth above regarding similarly identified features thus may not be repeated hereafter. Moreover, specific features of catheters and related components shown in FIGS. 1-4 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the catheter 200 and related components depicted in FIG. 5. Any suitable combination of the features, and variations of the same, described with respect to the catheter 100 and related components illustrated in FIGS. 1-4 can be employed with the catheter 200 and related components of FIG. 5, and vice versa. This pattern of disclosure applies equally to further embodiments depicted in subsequent figures and described hereafter, wherein the leading digits may be further incremented.

The catheter 200 of FIG. 5 includes a pressure sensor, a main lumen, and two separate lumens. The catheter 200 has two distal ports 232 located in a tip portion 250. In contrast with the catheter 100 of FIGS. 1-4, the catheter 200 has two proximal ports 222 located in the tip portion 250, instead of in the body portion 240. The catheter 200 also has a tip portion 250 that includes a tapered region 254 that reduces the diameter of the remainder of the tip portion 250 as compared to the diameter of the body portion 240. For example, the body portion 240 may have a diameter of about 5-7 French and the tip portion 250 may have a diameter of about 4-6 French.

The body portion 240 of the catheter 200 may be manufactured separately from the tip portion 250. This may facilitate the tip portion 250 of the catheter 200 comprising a more flexible material as compared to a more rigid body portion 240. For example, the body portion 240 may have a hardness of about 60-70 Shore D and the tip portion 250 may have a hardness of about 30-60 Shore A. The body portion 240 may be configured to provide pushability through a body lumen and sufficient torque transference to enable rotation of distal regions of the catheter 200 by manipulation that occurs adjacent the proximal end of the catheter 200. For example, the body portion 240 may be configured to provide more torque transference per unit of length than the tip portion 250. The body portion 240 may also comprise a structural support element, for example to increase the torque transference of the body portion 240.

The body portion 240 may have the same cross-sectional configuration as the tip portion 250 (e.g., similar to that illustrated in FIG. 2). Alternatively, the body portion 240 may have a different cross-sectional configuration, in which the lumens used in the tip portion 250 align with lumens in the body portion 240. Other cross-sectional configurations are also possible. A variety of coupling methods may be used to couple the body portion 240 to the tip portion 250, such as, for example, fusion, adhesion, and compression.

For example, the body portion 240 may comprise a central circular lumen with a plurality of partitioned lumens surrounding the central lumen. In that example, the body portion 240 may comprise a central tube coaxial with an outer tube that defines the outside of the body portion 240. Radially extending walls from the outer surface of the central tube to the inner surface of the outer tube may partition the space surrounding the central tube into separate lumens. A cross-section of that exemplary body portion 240 may comprise a "wagon wheel" with "spokes" (partition walls) extending from a "hub" (central tube) to an "outer rim" (outer tube), similar to the cross-sectional view provided in FIG. 10 and described in further detail below. The first and second separate lumens of the tip portion 250 may be coupled to two of the corresponding partitioned lumens of the wagon wheel body portion 240, and likewise the main lumen of the tip portion 250 may be coupled to the central tube of the wagon wheel body portion 240. The proximal end of the wagon wheel body portion 240 may be coupled to the single pressure readout device 160 (or any of the alternative readout devices discussed previously).

In the illustrated embodiment, the tip portion 250 does not include a curved distal region (e.g., a pigtail) before terminating at the end 256, but one could be present, as with the other differences between catheter 200 and catheter 100.

Additionally, a wire or other elongate member comprising a shape-memory material (e.g., a superelastic alloy) may be disposed within a lumen of the tip portion 250. For example, in some embodiments, a wire comprising Nitinol may be disposed within the first and/or second separate lumens of the tip portion 250. The shape-memory material may exert a force on the tip portion 250, causing the tip portion 250 to adopt a conformation that differs from the conformation that the tip portion 250 would adopt in the absence of the shape-memory material. Additionally or alternatively, in some embodiments, a wire (e.g., a shape-memory wire) disposed within the first and/or second separate lumens of the tip portion 250 may alter one or more characteristics of the tip portion 250. For example, the wire may increase the hardness and/or rigidity of the tip portion 250. For example, the wire may improve the pushability and/or torqueability of the tip portion 250. For example, the wire may increase the torque transference per unit length across the tip portion 250 and/or improve the longitudinal transfer of force across the tip portion 250 relative to comparable embodiments that lack the wire disposed within the first and/or second separate lumens of the tip portion 250. The wire may be removed once the tip portion 250 is positioned within a patient. In another example, a guidewire may be inserted in the main lumen, instead of, or in addition to, the first and second separate lumens.

The proximal end of the catheter 200 is not illustrated in FIG. 5. FIGS. 3 and 4 illustrate a possible proximal end of the catheter 200. As with the catheter 100, instead of a single pressure readout device 160, the alternative readout devices discussed above may be used as well.

For both the catheter 100 and the catheter 200, instead of two proximal ports and two distal ports in communication with the separate lumens, there may be only one proximal port and/or one distal port. Likewise, there may be multiple proximal ports and/or multiple distal ports.

Additionally, there may be any number of additional separate lumens formed along the length, or a portion thereof, of the catheter 100 and the catheter 200. These additional lumens may also have distal or proximal ports in communication with the lumens.

Methods of performing an interventional procedure are disclosed herein. For example, some methods disclosed herein may include the step of obtaining a catheter, such as any of catheters 100, 200 or variations thereof disclosed herein. Some methods further include the step of introducing a catheter into the vasculature of a patient, wherein the catheter comprises a main lumen and first and second separate lumens, and performing an interventional procedure comprising introducing or removing fluid from a main lumen of the catheter.

The methods may further comprise placing the first separate lumen in communication with blood of the patient at a distal location, placing the second separate lumen in communication with blood of the patient at a proximal location, and measuring pressure in the first and second separate lumens and thereby determining blood pressure of the patient at the distal location and the proximal location. The methods may further comprise determining the difference between the blood pressure of the patient at the distal location and the proximal location.

Performing the interventional procedure and measuring pressure may occur at the same time or sequentially, but can both be performed without removal of the catheter from the vasculature of the patient, if desired. For example, for a valvuloplasty procedure (a treatment for a stiff heart valve), a catheter (such as catheter 100 or catheter 200 or the variations thereof disclosed above) may be advanced from the groin of a patient (e.g., via femoral entry), through the aorta, and into the heart of the patient. The tip of the catheter may be advanced in between the leaflets of the stiff valve so that the first separate lumen is in communication with the blood of the patient on one side of the stiff valve (proximal location) and the second separate lumen is in communication with the blood of the patient on the other side of the valve (distal location). Before the valvuloplasty, the blood pressure on either side of the stiff valve may be monitored. A balloon portion of the catheter tip, aligned with the stiff valve, may then be inflated via the main lumen until the leaflets of the valve are opened. The balloon could optionally be inflated and deflated numerous times. After the balloon has been sufficiently deflated, the blood pressure on either side of the valve could be monitored to determine whether the valve was functioning better post-valvuloplasty. Depending upon the blood pressure results obtained, the valvuloplasty could then be performed again or the catheter removed from the patient's vasculature. Additionally, because the main lumen is separate from the lumens sensing the patient's blood pressure, the patient's blood pressure on either side of the valve could be monitored during the procedure as well. The methods and catheters disclosed herein could be used with a variety of interventional procedures.

Examples of introducing fluid from a main lumen of the catheter include introducing a contrast agent into the main lumen under high pressure or introducing a gas into the main lumen (such as for inflating a balloon portion of the catheter for balloon angioplasty, cutting balloon angioplasty, valvuloplasty, stent placement, shunt placement, or atherectomy, or for pneumatically operating a tool, such as a drill for rotoablation). Examples of removing fluid from a main lumen of the catheter include draining fluid from the patient through the main lumen and deflating a balloon. Other interventional procedures include delivering an electrical charge to a particular organ of the patient. Still further, gas may be introduced through any lumen of a catheter, such as a main lumen, a separate lumen, or any other lumen, to inflate a balloon or perform another procedure. Additionally, the main lumen may be used for pressure monitoring during a procedure wherein fluid is introduced through another lumen. For example, fluid may be introduced through a lumen other than the main lumen during a rotoablation procedure while the main lumen is utilized to measure pressure distal to the tool to detect possible occlusion from debris.

Methods of measuring blood pressure do not necessarily include an interventional procedure. For example, the methods may comprise introducing a catheter (such as catheter 100 or catheter 200 or the variations thereof disclosed above) into the vasculature of a patient, wherein the catheter comprises first and second separate lumens, placing the first separate lumen in communication with blood of the patient at a distal location, placing the second separate lumen in communication with blood of the patient at a proximal location, and measuring pressure in the first and second separate lumens and thereby determining blood pressure of the patient at the distal location and the proximal location.

In any of the methods of measuring blood pressure disclosed herein, the methods may further comprise determining the difference between the blood pressure of the patient at the distal location and the blood pressure at the proximal location. The methods may further comprise displaying that pressure differential. The methods may further comprise tracking pressure wave forms generated by the patient's heartbeats at the proximal and distal locations.

The methods may further comprise displaying on a single pressure readout device located at or near a proximal end of the catheter the blood pressure at the distal and proximal locations. The single pressure readout device may also measure pressure in the first and second separate lumens, thereby determining blood pressure of the patient at the distal location and the proximal location.

The methods may further comprise determining the presence of an occlusion in the first separate lumen, the second separate lumen, or both.

Figure 6:
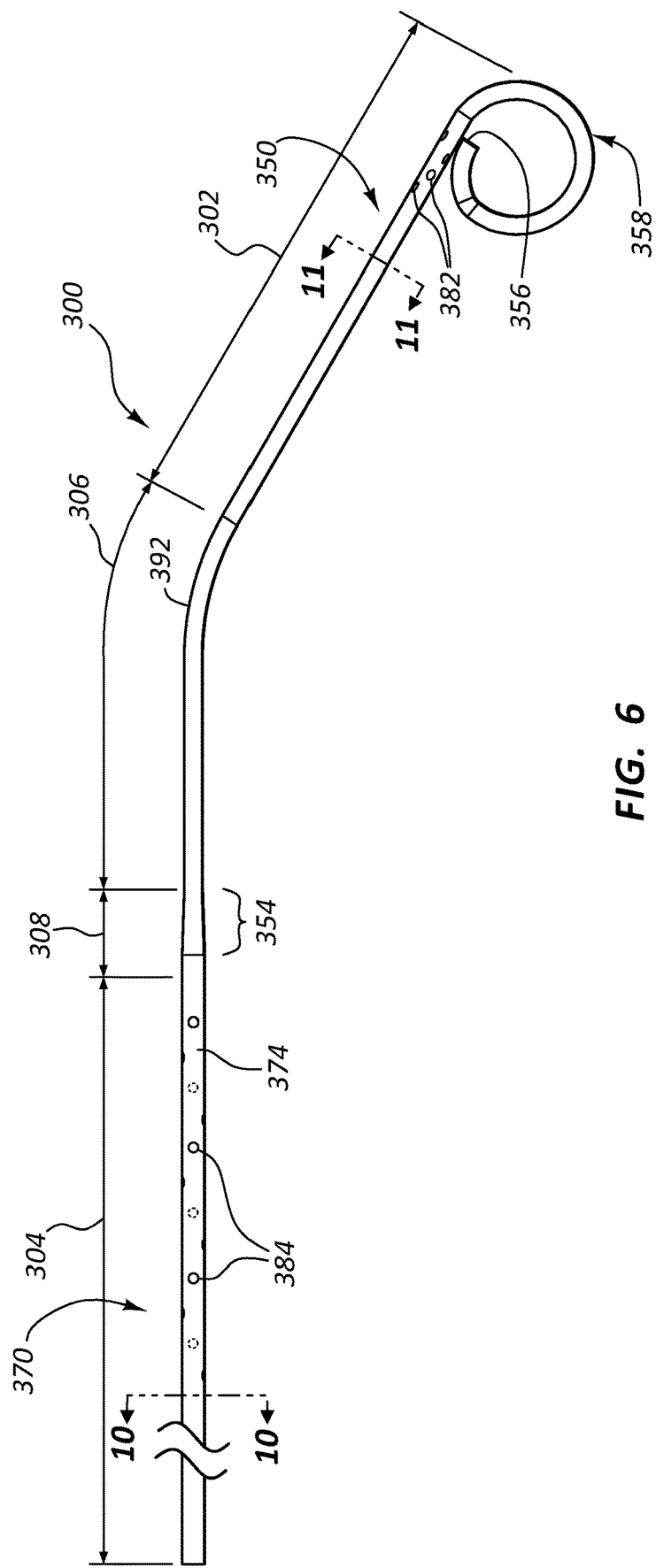
FIG. 6 is a side view of another embodiment of a catheter in an assembled state.

FIG. 6 provides a side view of an assembled catheter 300 according to another embodiment. The catheter 300 may comprise an elongate catheter body 370 and an elongate catheter tip 350 that is coupled to the elongate catheter body 370. The catheter tip 350 may comprise an opening at its distal end 356 and/or one or more side ports 382 that are in fluid communication with a first lumen that extends through the catheter tip 350. The catheter tip 350 may also comprise a curved distal region 358 that is configured to facilitate atraumatic advancement of the catheter tip 350 within a lumen of a patient. For example, the curved distal region 358 of the catheter tip 350 may adopt a rounded (e.g., pigtail) conformation such that, as the catheter 300 is advanced within the lumen of the patient, body lumen surfaces are initially contacted by a curved surface rather than the blunt distal end 356 of the catheter 300.

The catheter tip 350 may be coupled to the elongate catheter body 370 adjacent the distal end of the elongate catheter body 370. The elongate catheter body 370 may comprise a first elongate tube 374 with one or more side ports 384 that are configured to allow fluid to enter into one or more lumens. In some embodiments, the one or more side ports 384 include a plurality of ports that spiral helically around the catheter 300.

In some embodiments, the first elongate tube 374 comprises a diameter of 5-7 French and the catheter tip comprises a diameter of 4-6 French. In some embodiments, the catheter 300 comprises a tapered region 354. The tapered region 354 may include a portion of the elongate catheter body 370 and/or a portion of the catheter tip 350. In the embodiment depicted in FIG. 6, the tapered region 354 comprises a distal end and a proximal end. The distal end of the tapered region may have a smaller outer diameter than the proximal end of the tapered region 354. For example, in some embodiments, the tapered region may taper from an outer diameter of 0.075-0.100 inches at the proximal end to an outer diameter of 0.06-0.07 inches at the distal end. In some embodiments, the tapered region tapers from a diameter of 5-7 French to a diameter of 4-6 French. For example, the tapered region may taper from a diameter of 6 French to a diameter of 5 French. In some embodiments, the tapered region may continuously taper over a length of 0.250-0.500 inches. Stated differently, in some embodiments, the outer diameter of the proximal portion 304 is greater than the outer diameter of the intermediate portion 306 and/or the outer diameter of the distal portion 302 of the catheter 300. In other or further embodiments, the outer diameter of the intermediate portion 306 is substantially the same as the outer diameter of the distal portion 302.

The catheter 300 may include a distal portion 302, a proximal portion 304, and an intermediate portion 306 disposed between the proximal portion 304 and the distal portion 302. The distal portion 302 may have at least one port (e.g., distal ports 382) that is in fluid communication with a first lumen 365 of the catheter 300 (see FIGS. 10 and 11). As shown in FIG. 6, the proximal portion 304 may have at least one port (e.g., proximal ports 384) that is in fluid communication with a second lumen (e.g., a radial lumen 396) of the catheter 300. In some embodiments, the intermediate portion 306 does not contain any ports. In some embodiments, the catheter 300 may further include a transition portion 308 that is disposed between the proximal portion 304 and the intermediate portion 306. In some embodiments, the transition portion 308 may correspond to (or roughly correspond to) the tapered region 354. In some embodiments, the tapered region 354 is longer or shorter than the transition portion 308. Some embodiments may lack a tapered region altogether.

In some embodiments, the distal portion 302 extends from a distal end 356 of the catheter 300 to the intermediate portion 306 of the catheter 300. The intermediate portion 306 of the catheter may extend from the proximal end of the distal portion 302 to a transition portion 308 between the intermediate portion 306 and the proximal portion 304. The proximal portion 304 may extend from the transition portion 308 to adjacent the proximal end of the catheter 300. In some embodiments, the intermediate portion 306 includes a bend 392 (or a plurality of bends) when the catheter 300 is in an unconstrained state. The position and/or structure of the bend(s) may be altered for any number of purposes. For example, the distance between bends, the angle(s) traversed by one or more of the bends, and the number of bends may be altered based on the intended use of the catheter, the anatomy of the patient, etc. In some embodiments, the intermediate portion 306 forms an angle of between 130° and 170° (or more particularly between 140° and 160°) when the catheter is in an unconstrained state. Stated differently, straight portions of the catheter 300 may be disposed at an obtuse angle of between 130° and 170° (and/or between 140° and 160°) when the catheter 300 is in an unconstrained state.

In some embodiments, the elastomeric material of the catheter 300 may be predisposed to adopt a curved configuration, thereby forming (or contributing to) a bend 392 in the catheter 300. In other or further embodiments, a shape-memory material (e.g., nitinol) may form (or contribute to) a bend 392 in the catheter 300. The shape-memory material may thus exert a force on the catheter 300, causing the catheter 300 to adopt a curved conformation that differs from the conformation that the catheter 300 would adopt in the absence of the shape-memory material.

The distal portion 302 may have a first radiodensity, the proximal portion 304 may have a second radiodensity, and the intermediate portion 306 may have a third radiodensity.

In some embodiments, the third radiodensity differs from both the first radiodensity and the second radiodensity. For example, in some embodiments, the intermediate portion 306 is less radiodense than both the distal portion 302 and the proximal portion 304. In other embodiments, the intermediate portion 306 is more radiodense than both the distal portion 302 and the proximal portion 304. In some embodiments, the radiodensity of the distal portion 302, the proximal portion 304, and the intermediate portion 306 are each different from one another. In other embodiments, the radiodensity of the distal portion 302 and the proximal portion 304 are substantially the same.

Some embodiments in which the radiodensity of the intermediate portion 306 differs from the radiodensity of both the proximal portion 304 and the distal portion 302 may facilitate proper placement of the catheter 300 during an interventional procedure. For example, the catheter 300 may be inserted into a patient to measure pressure differences across a heart valve during a medical procedure. As the practitioner inserts the catheter 300 into the patient and toward the heart valve, the location of the catheter 300 may be tracked by radiographic imaging. More particularly, the practitioner may advance the catheter 300 within the patient while viewing radiopaque portions of the catheter 300 until the proximal portion 304 of the catheter 300 is disposed proximal of the valve while the distal portion 302 of the catheter 300 is disposed distal of the valve. For example, in some embodiments in which the proximal portion 304 and the distal portion 302 have a greater radiodensity than the intermediate portion 306, the practitioner may, as determined by radiographic imaging, advance the catheter 300 within the patient until the radiopaque distal portion 302 is disposed distal of the valve, the radiolucent intermediate portion 306 is disposed across the valve, and the radiopaque proximal portion 304 is disposed proximal of the valve.

In some embodiments, one or more elements or portions of the catheter 300 may be of different hardness. For example, in some embodiments, the catheter tip 350 (which may form both the distal portion 302 and the intermediate portion 306) comprises an elastomer that renders the catheter tip 350 "softer" and/or more flexible than the elongate catheter body 370. In some embodiments, the catheter tip 350 includes a polyether block amide, such as PEBAX. A relatively soft and/or flexible catheter tip may, alone or in combination with a curved distal region 358, facilitate atraumatic advancement of the catheter 300 through a body lumen and/or facilitate traversal of a curved path.

The elongate catheter body 370 may comprise a set of material properties that differs from the material properties of the elongate catheter tip 350. For example, the elongate catheter body 370 may be harder and/or stiffer than the catheter tip 350. The elongate catheter body 370 may be configured to provide pushability through a body lumen and sufficient torque transference to enable rotation of distal regions of the catheter 300 by manipulation that occurs adjacent the proximal end of the catheter body 370. In some embodiments, the elongate catheter body 370 is configured to provide more torque transference per unit of length than the elongate catheter tip 350.

In some embodiments, the proximal portion 304 of the catheter 300 has a durometer hardness that is greater than a durometer hardness of the distal portion 302. In other or further embodiments, the intermediate portion 306 has a durometer hardness that is greater than the durometer hardness of the distal portion 302. In still other or further embodiments, the proximal portion 304 may have a durometer hardness that is greater than the durometer hardness of the intermediate portion 306. More particularly, in some embodiments, the distal portion 302 of the catheter 300 has a durometer hardness of between 45 and 55 Shore D, the intermediate portion 306 has a durometer hardness of between 65 and 80 Shore D, and the proximal portion 304 has a durometer hardness of between 90 and 100 Shore D. In some embodiments, one or both of the intermediate portion 306 and the distal portion 302 includes a polyether block amide, such as PEBAX.

The hardness of various portions 302, 304, 306, 308 may provide pushability through a body lumen and sufficient torque transference to enable rotation of distal regions of the catheter 300 by manipulation that occurs adjacent the proximal end of the catheter body 370. In some embodiments, the proximal portion 304 is configured to provide more torque transference per unit of length than the intermediate portion 306 and/or the distal portion 302.

In some embodiments, the catheter 300 is sized and shaped to facilitate measurement of differences in blood pressure across a heart valve of a human patient when the catheter 300 has been inserted into the patient via a femoral access point.

Figure 7:
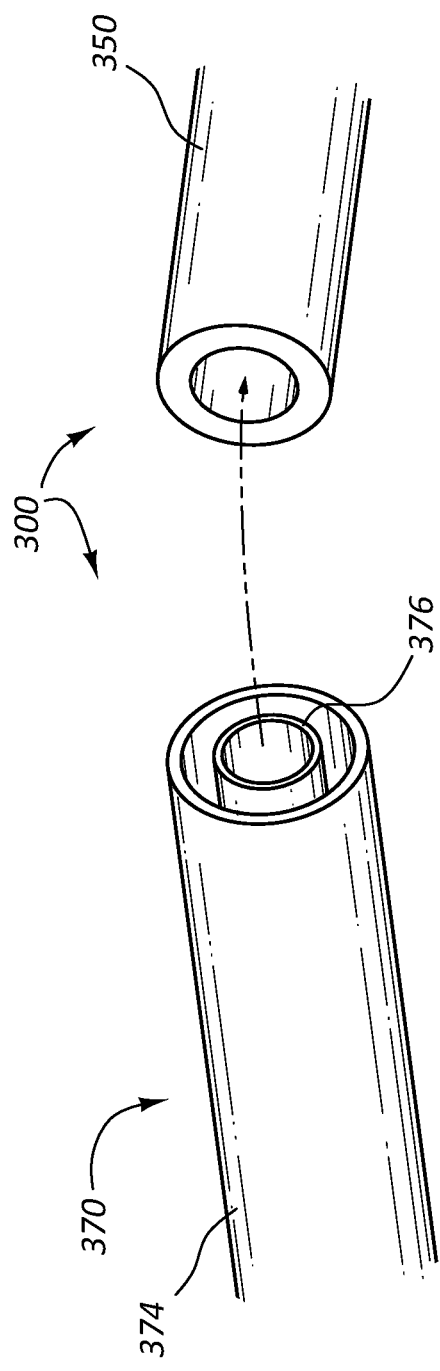
FIG. 7 is a perspective view of a portion of the catheter of FIG. 6 in a disassembled state.
Figure 8:
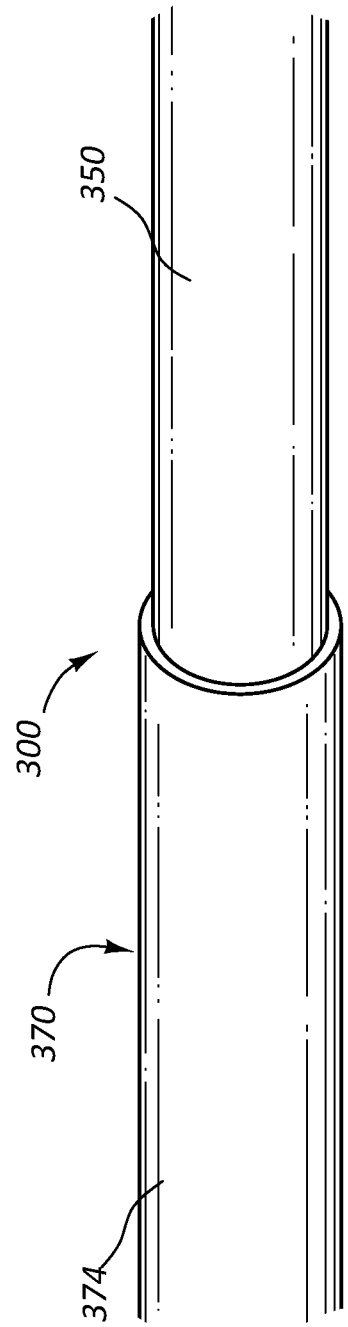
FIG. 8 is a perspective view of a portion of the assembled catheter of FIG. 6.

FIGS. 7 and 8 provide perspective views of a portion of the catheter 300 in a disassembled state (FIG. 7) and an assembled state (FIG. 8). In the disassembled state shown in FIG. 7, the catheter tip 350 is not coupled to the elongate catheter body 370. In the assembled state shown in FIG. 8, the catheter tip 350 is coupled to the elongate catheter body 370. With reference to FIGS. 7 and 8, the elongate catheter body 370 may comprise a first elongate tube 374, a second elongate tube 376, and septal walls (not shown). The second elongate tube 376 may be at least partially disposed within the first elongate tube 374. The first elongate tube 374 and the second elongate tube 376 may form at least a portion of the proximal portion 304 of the catheter 300.

The first elongate tube 374 may be a generally cylindrical structure. In some embodiments, the first elongate tube 374 comprises an elastomer, such as nylon.

The second elongate tube 376 may be a generally cylindrical structure. The second elongate tube 376 may be disposed within the first elongate tube 374 such that the second elongate tube 376 is coaxial to the first elongate tube 374. In the embodiment depicted in FIGS. 7 and 8, the distal ends of the first elongate tube 374 and the second elongate tube 376 are flush with one another. In other embodiments, the distal end of the second elongate tube 376 may extend beyond the distal end of the first elongate tube 374. In still other embodiments, the distal end of the first elongate tube 374 may extend beyond the distal end of the second elongate tube 376, such as described in U.S. patent application Ser. No. 14/674,143, titled CATHETER WITH CATHETER TIP AND RELATED METHODS, which is hereby incorporated by reference in its entirety.

With reference to FIGS. 7 and 8, the second elongate tube 376 may comprise an elastomer, such as nylon. In some embodiments, the second elongate tube 376 comprises a liner or other material to increase the hardness, stiffness, pressure capacity, and/or durability of the second elongate tube 376. For example, the second elongate tube 376 may comprise steel braids and/or a layer comprising polyimide. More particularly, in some embodiments, the second elongate tube 376 comprises a nylon tube with a polyimide liner disposed on the inner diameter of the nylon tube.

The catheter tip 350 may comprise a proximal portion that is configured to be coupled adjacent the distal end of the elongate catheter body 370 by disposing the proximal portion of the catheter tip 350 between the first elongate tube 374 and the second elongate tube 376 and subsequently fusing the proximal portion to both the first elongate tube 374 and the second elongate tube 376. In this manner, the proximal portion of the catheter tip 350 may be disposed around a portion of the second elongate tube 376 and disposed within a distal portion of the first elongate tube 374. When the catheter tip 350 is coupled to the elongate catheter body 370, a first lumen 365 (see FIG. 9) may extend through both the second elongate tube 376 and the elongate catheter tip 350.

Figure 9:
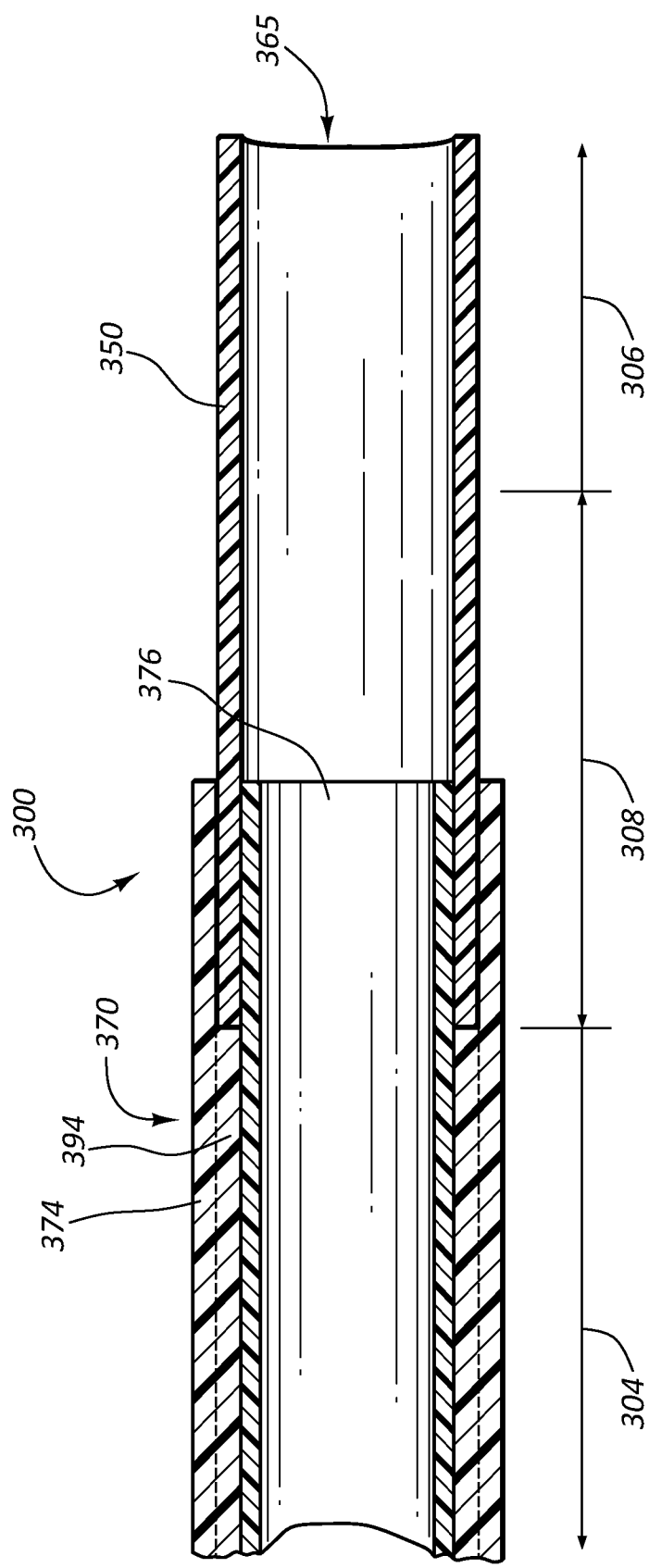
FIG. 9 is a cross-sectional side view of a portion of the assembled catheter of FIG. 6.
Figure 10:
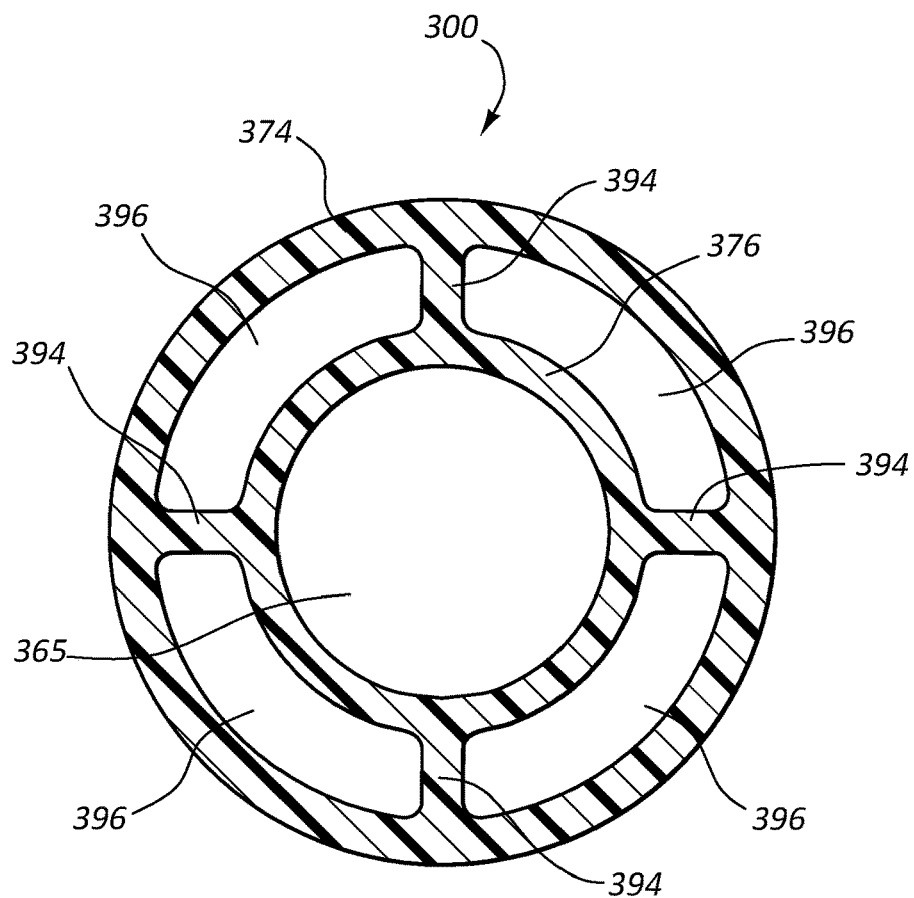
FIG. 10 is a cross-sectional view of the catheter of FIG. 6 taken through line 10-10 of FIG. 6.

FIG. 9 provides a cross-sectional side view of a portion of the assembled catheter of FIG. 6. This figure is intended to schematically illustrate both the structure of a portion of the catheter 300 and methods that may be used to couple a catheter tip 350 to a catheter body 370. The particular structure, shape, or arrangement of components depicted in this figure is not meant to limit the scope of this disclosure. FIG. 10 provides a cross-sectional view of the elongate catheter body 370 of the catheter 300 taken through line 10-10 of FIG. 6.

The portion of the catheter 300 depicted in FIG. 9 includes some of the intermediate portion 306, an entirety of the transition portion 308, and some of the proximal portion 304 of the catheter 300. Stated differently, FIG. 9 shows a catheter tip 350 with a proximal portion of the catheter tip 350 disposed between the first elongate tube 374 and the second elongate tube 376 of an elongate catheter body 370. The catheter tip 350 may be generally tubular in shape and configured to couple to the elongate catheter body 370. The catheter 300 may comprise a first lumen 365, such as a central lumen, that extends through both the second elongate tube 376 and the catheter tip 350 (or at least through a portion of each) when the catheter 300 is in an assembled state.

With reference to FIGS. 9 and 10, the elongate catheter body 370 may comprise a first elongate tube 374, a second elongate tube 376, and a plurality of septal walls 394. The plurality of septal walls 394 may extend radially inward from the first elongate tube 374 to the second elongate tube 376 along a first length of the first elongate tube 374. In some embodiments, the first length does not extend to the distal end of the first elongate tube 374. The plurality of septal walls 394, the first elongate tube 374, and the second elongate tube 376 may together define (in whole or in part) two or more radial lumens 396 disposed between the first elongate tube 374 and the second elongate tube 376. In the depicted embodiment, the plurality of radial lumens 396 are disposed proximal of the intermediate portion 306 and the transition portion 308 of the catheter 300.

As shown in FIG. 9, a proximal portion of the catheter tip 350 may be disposed between the first elongate tube 374 and the second elongate tube 376. With the proximal portion of the catheter tip 350 disposed between these components, the proximal portion of the catheter tip 350 may be fused to the elongate catheter body 370 via fusion to one or more of the second elongate tube 376, the first elongate tube 374, and the septal walls 394. Such fusion may be accomplished in various ways, for example, (1) by applying heat to the elongate catheter body 370 and/or catheter tip 350 (or portions thereof), and/or (2) through the use of one or more adhesives or other chemical fasteners (e.g., a solvent that softens or partially dissolves catheter components).

In some embodiments, fusion causes adjacent materials to blend. For example, upon fusion of one or more of the second elongate tube 376, the first elongate tube 374, and septal walls 394 to a portion of the catheter tip 350, material positioned adjacent the interface of these components may blend to some degree across a fusion interface (i.e., the post-fusion region (or regions) of a catheter 300 that consist of blended material from both the catheter tip 350 and one or more components of the elongate catheter body 370, for example the first elongate tube 374, the second elongate tube 376 and/or the septal walls 394). In some embodiments, blending occurs across the entire thickness of a catheter tip 350 wall. In other embodiments, blending occurs only near the interface such that the catheter tip 350 comprises a layer that does not include material blended from the first elongate tube 374 or the second elongate tube 376. Blending may produce a tapered region 354 to provide a smooth transition between the larger diameter of the first elongate tube 374 and the second elongate tube 376, as shown in FIG. 6.

As shown in FIG. 10, which provides a cross-sectional view of the elongate catheter body 370 of the catheter 300 taken through line 10-10 of FIG. 6, the elongate catheter body 370 may comprise a first elongate tube 374, a second elongate tube 376, and septal walls 394. The second elongate tube 376 may define, at least in part, a first lumen 365. The first elongate tube 374, the second elongate tube 376, and the septal walls 394 may define (in whole or in part) one or more radial lumens 396. The first lumen 365 may be centrally disposed such that the radial lumens 396 are peripherally disposed around the first lumen 365.

The first elongate tube 374 may be generally cylindrical in shape and comprise a wall that is 0.003-0.010 inches thick. The second elongate tube 376 may also be generally cylindrical in shape and comprise a wall that is 0.003-0.010 inches thick. In some embodiments, the wall of the second elongate tube 376 comprises a layer (e.g., a polyimide layer) with a thickness of 0.001-0.0035 inches.

The septal walls 394 may extend radially inward from the first elongate tube 374 to the second elongate tube 376. In this manner, the septal walls 394 may fixedly dispose at least a portion of the second elongate tube 376 within the first elongate tube 374. An elongate catheter body 370 may comprise any number of septal walls 394 (e.g., 1, 2, 3, 4, or 5). Each septal wall 394 may have a thickness of 0.003-0.007 inches and/or a height (i.e., the distance from the first elongate tube 374 to the second elongate tube 376) of 0.005-0.017 inches.

In some embodiments, the first elongate tube 374, the second elongate tube 376, and the septal walls 394 (or portions of these components) are integrally formed via extrusion. For example, in some embodiments, an elastomer (e.g., nylon) or other material is pushed or drawn through a die to form a portion of a catheter 300 with a fixed cross-sectional profile. This portion of the catheter 300 may comprise a portion of the first elongate tube 374, a portion of the second elongate tube 376, and a portion of the septal walls 394.

A first lumen 365 may be at least partially defined by the second elongate tube 376. In some embodiments, the first lumen 365 comprises a diameter of 0.030-0.050 inches. This main lumen 365 may be in fluid communication with an opening at the distal end 356 and/or one or more distal ports 382, such as the plurality of ports 382 that helically spiral around the catheter 300 as depicted FIG. 6. Under some circumstances, when the catheter 300 is disposed within a body lumen, fluid may enter into the first lumen 365 through the distal opening at the distal end 356 and/or through one or more distal ports 382. Such fluid may flow toward the proximal end of the catheter 300. By coupling the first lumen 365 to a pressure sensor, body fluid pressure (e.g., blood pressure) may be measured. Other sensors may be used to detect and/or measure other characteristics of the body fluid.

One or more radial lumens 396 may be defined, in whole or in part, by the septal walls 394, the first elongate tube 374, and the second elongate tube 376. In some embodiments, the one or more radial lumens 396 extend proximally from a fused region of the catheter 300 (i.e., the region over which the elongate catheter body 370 and the catheter tip 350 are fused together). Additionally or alternatively, in some embodiments (e.g., embodiments where the septal walls 394 do not extend to the proximal end of the elongate catheter body 370), multiple radial lumens 396 may combine adjacent the proximal end of the elongate catheter body 370. Under some circumstances, when a catheter 300 is disposed within a body lumen, body fluid within the body lumen may enter into the one or more radial lumens 396 via one or more side ports 384 (see FIG. 6). Such fluid may flow toward the proximal end of the catheter 300. By coupling the one or more radial lumens 396 to a pressure sensor, body fluid pressure (e.g., blood pressure) may be measured. Other sensors may be used to detect and/or measure other characteristics of the body fluid. In some embodiments, the one or more radial lumens 396 are not in fluid communication with the first (e.g., main) lumen 365.

In some embodiments and circumstances, differences may be detected and/or measured between fluid that enters into a first lumen 365 and fluid that enters into one or more other lumens (e.g., radial lumens 396) disposed between the first elongate tube 374 and the second elongate tube 376. For example, by coupling each of the main lumen 365 and one or more of the radial lumens 396 to one or more pressure sensors, the fluid pressures within each lumen may be measured and compared. Such comparisons may be useful in monitoring blood pressure across a valve (e.g., a heart valve during a valvuloplasty procedure). In some embodiments, a pressure within the first lumen 365 and/or a second lumen (e.g., a radial lumen 396), a difference of pressure between the lumens, and/or a combination thereof are displayed on a pressure readout device analogous to the pressure readout device 160 discussed above. Stated differently, in some embodiments, the catheter 300 may include a pressure readout device that is in communication with one or more pressure sensors.

Figure 11:
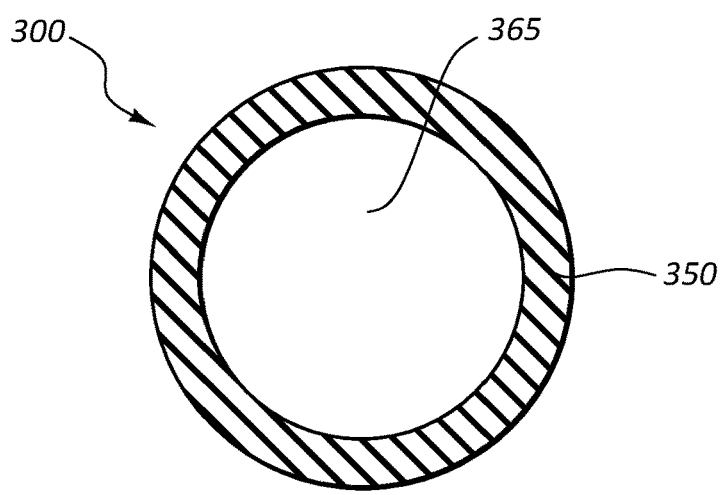
FIG. 11 is a cross-sectional view of the catheter of FIG. 6 taken through line 11-11 of FIG. 6.

FIG. 11 provides a cross-sectional view of the catheter 300 of FIG. 6 taken through line 11-11 of FIG. 6. As shown in FIG. 11, the first lumen 365 may be defined, at least in part, by the inner diameter of the catheter tip 350.

Figure 12:
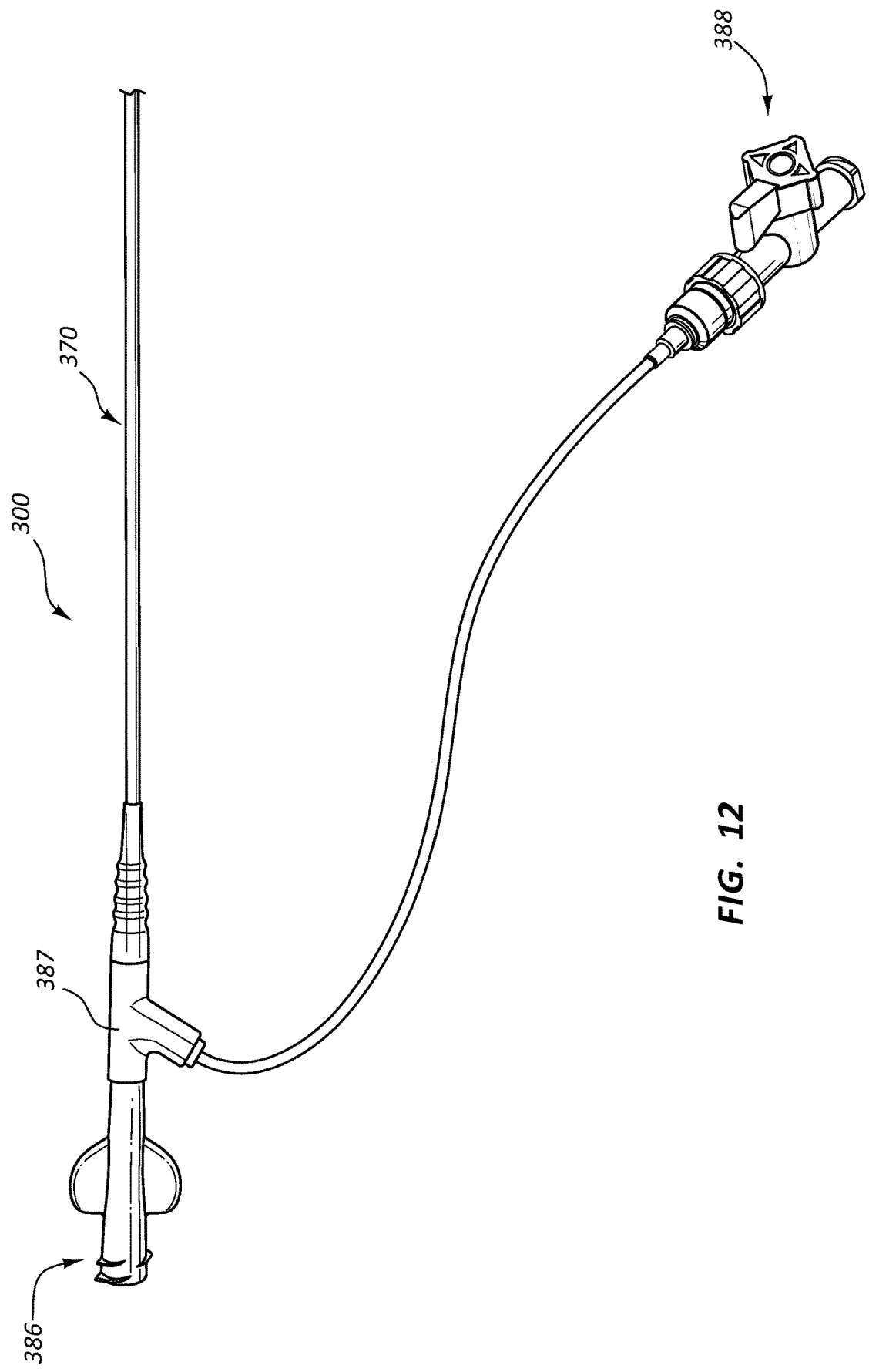
FIG. 12 is a perspective view of a portion of the catheter of FIG. 6 showing connections adjacent the proximal end of the catheter.

FIG. 12 provides a perspective view of a portion of the catheter 300 of FIG. 6 showing connections adjacent the proximal end of the catheter 300. In the depicted embodiment, the elongate catheter body 370 of the catheter 300 is coupled to a first connector 386 and a second connector 388 via a branched connector 387. In some embodiments, the first connector 386 is in fluid communication with fluid in a first (e.g., main or central) lumen 365 of the catheter, while the second connector 388 is in fluid communication with a second lumen (e.g., one or more radial lumens 396) of the catheter 300. One of ordinary skill in the art, with the benefit of this disclosure, will understand that various different connections and configurations may be employed adjacent the proximal end of the catheter 300. Stated differently, the particular structure, shape, or arrangement of components depicted in FIG. 12 is not meant to limit the scope of this disclosure.

Figure 13:
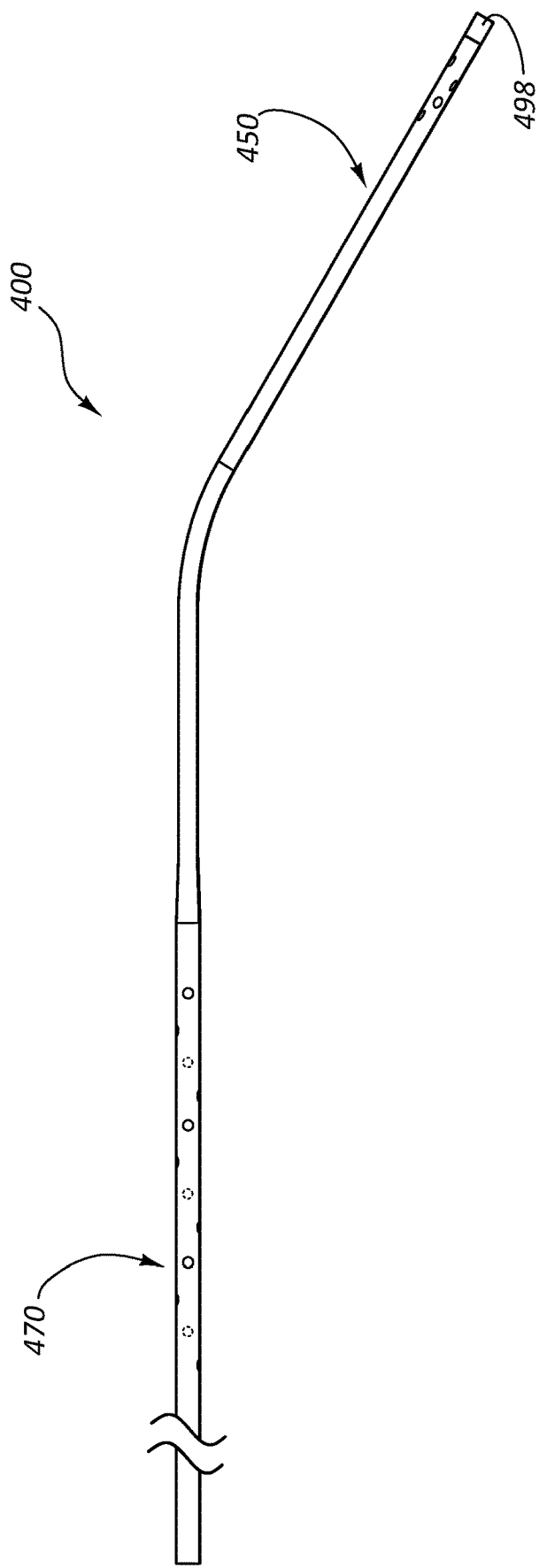
FIG. 13 is a perspective view of a catheter according to another embodiment.

FIG. 13 provides a side view of a catheter 400 according to another embodiment. The catheter 400 is generally analogous to the catheter 300 described above with reference to FIGS. 6-12. For instance, the catheter 400 includes an elongate body 470 and a tip portion 450 that are generally analogous to the elongate body 370 and tip portion 350 of the catheter 300. However, in contrast to the catheter 300 described in FIGS. 6-12, the catheter 400 lacks a curved distal region. Instead, the catheter 400 includes a flexible terminal portion 498 that is disposed distal of the distal portion 402. In some embodiments, the terminal portion 498 may be softer and/or more flexible than the distal portion 402. In some embodiments, the terminal portion 498 has a hardness of between 30 and 40 Shore D. In some embodiments, the terminal portion is between 2 and 3 mm in length. The terminal portion 498 may facilitate atraumatic advancement of the catheter 400 within a patient.

Methods of performing an interventional procedure are disclosed herein. In some embodiments, a method for performing an interventional procedure may include the step of obtaining a catheter, such as any of the catheters disclosed herein. The method may further include the step of introducing the catheter into the vasculature of the patient (e.g., via a femoral access point) such that the first lumen is in fluid communication with blood of the patient at a distal location and the second lumen is in fluid communication with blood of the patient at a proximal location. More particularly, in some embodiments, the step of introducing the catheter into the vasculature of the patient involves inserting the catheter into the patient such that the distal location is on a first side of a blockage or heart valve and the proximal location is on a second side of the blockage or heart valve.

For example, during an aortic valvuloplasty procedure, a catheter may be inserted into the radial or femoral artery of a patient and advanced within the patient's vasculature and heart such that a first lumen of the catheter is in primary fluid communication with blood on one side of the aortic valve (e.g., blood in the left ventricle) and a second lumen is in primary fluid communication with blood on the other side of the valve (e.g., blood in the aorta). More particularly, one or more distal openings (e.g., ports) of a catheter may be in primary fluid communication with a first lumen of a catheter and one or more proximal openings (e.g., ports) may be in primary fluid communication with a second lumen of a catheter. When the catheter is positioned in this manner, fluid from each side of the valve may enter into the corresponding lumen.

In some embodiments, once the catheter is placed within the patient, the practitioner may measure pressure in both the first and second lumens. From these measurements, a difference in fluid pressure may be calculated. Stated differently, by coupling each of the first and second lumens to a pressure sensor, the practitioner may measure the fluid pressure inside the first lumen and the second lumen. From this data, the relative and/or absolute blood pressure on each side of the valve may be measured and compared.

FIG. 14 provides a perspective view of a removable gripping member 50 for manipulating a catheter 500. As shown in FIG. 14, the gripping member 50 includes a flared proximal end 52, a flared distal end 54, and a midsection 56 disposed between the flared proximal end 52 and the flared distal end 54. The gripping member 50 further includes a lumen 60 that that may be accessed via a slot 70 in the gripping member 50. The lumen 60 and slot 70 may be sized and shaped to allow insertion of a proximal portion 504 of the catheter into the lumen 60 of the gripping member 50. Once the proximal portion 504 of the catheter 500 is disposed within the lumen 60 of the gripping member 50, the gripping member 50 may frictionally engage (e.g., via an interference fit) with the proximal portion 504 of the catheter 500.

The gripping member may be made from any suitable material. For example, in some embodiments, the gripping member 50 is made from an elastomeric material (e.g., a thermoplastic elastomer).

In some embodiments, the gripping member may further include a tab 80. The tab 80 may be configured to facilitate the application of torque to the gripping member 50. The application of torque to the gripping member 50 may, in turn, apply torque to the catheter 500.

The gripping member 50 may be used in connection with a catheter, such as any of catheters 100, 200, 300, 400, or 500 described herein. For example, during a medical procedure, a practitioner may obtain a catheter (e.g., catheter 500 of FIG. 14) and insert a portion of the catheter 500 into a patient 5 such that a proximal end of the catheter 500 remains outside of the patient 5. The practitioner may then selectively grip a proximal portion 504 of the catheter 500 with the removable gripping member 50 such that the removable gripping member 50 is distal of the proximal end of the catheter 500. The practitioner may then rotate the removable gripping member 50 (e.g., by rotating the tab 80 about a longitudinal axis of the gripping member 50) to apply torque to the catheter 500. Rotating the removable gripping member 50 in this manner may provide increased torque transference to a distal end of the catheter 500 relative to rotating the proximal end of the catheter 500. Stated differently, by allowing the practitioner to grasp a proximal portion 504 of the catheter 500 at a location that is distal of the proximal end of the catheter 500, the gripping member 50 may provide increased torque transference and/or pushability.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A catheter comprising:
   a body portion comprising:
      a main lumen centrally disposed along the body portion;
      a first lumen disposed radially outward from the main lumen;
      a second lumen disposed radially outward from the main lumen opposite the first separate lumen;
      a distal portion having at least one port that is in fluid communication with the first lumen of the catheter, wherein the distal portion has a first radiodensity;
      a proximal portion having at least one port that is in fluid communication with the second lumen of the catheter, wherein the proximal portion has a second radiodensity; and
      an intermediate portion disposed between the proximal portion and the distal portion, the intermediate portion having a third radiodensity; and
   an integrated pressure readout housing disposed at a proximal end of the body portion;
   wherein the proximal end of the body portion terminates in a main proximal conduit that comprises the main lumen, a first conduit that comprises the first lumen, and a second conduit that comprises the second lumen, wherein a portion of each conduit is disposed within the integrated pressure readout housing and a portion of each conduit is disposed outside of the integrated pressure readout housing;
   wherein a first inline pressure sensor is disposed within the integrated pressure readout housing and is in communication with the first lumen of the first conduit and a second inline pressure sensor is disposed within the integrated pressure readout housing and is in communication with the second lumen of the second conduit;
   wherein the third radiodensity differs from both the first radiodensity and the second radiodensity;
   wherein the intermediate portion comprises a bend when the catheter is in an unconstrained state; and
   wherein the third radiodensity facilitates positioning the intermediate portion across a heart valve.

2. The catheter of claim 1, wherein the first lumen and the second lumen are not in fluid communication with one another.

3. The catheter of claim 1, wherein the intermediate portion is less radiodense than both the distal portion and the proximal portion.

4. The catheter of claim 1, wherein the intermediate portion is more radiodense than both the distal portion and the proximal portion.

5. The catheter of claim 1, wherein the bend of the intermediate portion forms an angle of between 130° and 170° when the catheter is in the unconstrained state.

6. The catheter of claim 1, further comprising a first elongate tube and a second elongate tube that is at least partially disposed within the first elongate tube, wherein the first elongate tube and the second elongate tube form at least a portion of the proximal portion of the catheter.

7. The catheter of claim 6, further comprising:
   a plurality of septal walls extending radially inward from the first elongate tube to the second elongate tube; and
   a plurality of radial lumens defined, at least in part, by the plurality of the septal walls, wherein the plurality of radial lumens is disposed proximal of the intermediate portion and between the first elongate tube and the second elongate tube.

8. The catheter of claim 7, further comprising:
   an elongate tubular catheter tip that forms at least a portion of the intermediate portion; and
   a transition portion between the proximal portion of the catheter and the intermediate portion of the catheter, wherein the transition portion comprises a portion of the catheter tip that is disposed between and fused to both the first elongate tube and the second elongate tube.

9. The catheter of claim 1, wherein:
   the proximal portion comprises a plurality of ports that spiral helically around the proximal portion; and
   the plurality of ports of the proximal portion includes the at least one port that is in fluid communication with the second lumen of the catheter.

10. The catheter of claim 1, wherein the first inline pressure sensor and the second inline pressure sensor comprise a pressure transducer.

11. The catheter of claim 10, wherein the pressure transducer comprises a metal band configured to expand or contract in response to pressure changes within the first and/or second lumens, wherein the expansion and contraction changes the electrical resistance of the metal.

12. The catheter of claim 1, wherein the pressure readout housing comprises a display to display the pressure values measured by the first inline pressure sensor and the second inline pressure sensor.

13. A method of performing an interventional procedure, the method comprising:
   obtaining the catheter of claim 1;
   introducing the catheter into a vasculature of a patient such that the first lumen is in fluid communication with blood of the patient at a distal location and the second lumen is in fluid communication with blood of the patient at a proximal location; and
   measuring pressure in both the first and second lumens.

14. The method of claim 13, wherein introducing the catheter into the vasculature of the patient comprises inserting the catheter into the patient such that the distal location is on a first side of a heart valve and the proximal location is on a second side of the heart valve.

15. A catheter comprising:
   a body portion comprising:
      a main lumen centrally disposed along the body portion,
      a first lumen disposed radially outward from the main lumen,
      a second lumen disposed radially outward from the main lumen opposite the first lumen,
      a distal portion having at least one port that is in fluid communication with the first lumen of the catheter, wherein the distal portion has a first durometer hardness;
      a proximal portion having at least one port that is in fluid communication with the second lumen of the catheter, wherein the proximal portion has a second durometer hardness; and
      an intermediate portion disposed between the proximal portion and the distal portion, the intermediate portion having a third durometer hardness;
   an integrated pressure readout housing disposed at a proximal end of the body portion;
   wherein the proximal end of the body portion terminates in a main proximal conduit that comprises the main lumen, a first conduit that comprises the first lumen, and a second conduit that comprises the second lumen, wherein a portion of each conduit is disposed within the integrated pressure readout housing and a portion of each conduit is disposed outside of the integrated pressure readout housing;

wherein a first inline pressure sensor is disposed within the integrated pressure readout housing and is in communication with the first lumen of the first conduit and a second inline pressure sensor is disposed within the integrated pressure readout housing and is in communication with the second lumen of the second conduit;

wherein the first durometer hardness is between 45 and 55 Shore D, the second durometer hardness is between 90 and 100 Shore D, and the third durometer hardness is between 65 and 80 Shore D; and a transition zone disposed between the proximal portion and the intermediate portion, wherein the transition zone comprises:
- a proximal portion inner tube, a proximal portion outer tube, and an annular space disposed between the proximal portion inner tube and the proximal portion outer tube; and
- a proximal end portion of the intermediate portion, wherein the proximal end portion is disposed in the annular space and fixedly coupled to the proximal portion inner tube and the proximal portion outer tube.

16. The catheter of claim 15, further comprising a terminal portion disposed distal of the distal portion, wherein the terminal portion has a durometer hardness of between 30 and 40 Shore D.

17. The catheter of claim 15, further comprising a first elongate tube and a second elongate tube that is at least partially disposed within the first elongate tube, wherein the first elongate tube and the second elongate tube form at least a portion of the proximal portion of the catheter.

18. The catheter of claim 17, further comprising:
- a plurality of septal walls extending radially inward from the first elongate tube to the second elongate tube; and
- a plurality of radial lumens defined, at least in part, by the plurality of the septal walls, wherein the plurality of radial lumens is disposed proximal of the intermediate portion and between the first elongate tube and the second elongate tube.

\* \* \* \* \*